(12) United States Patent
Luciano et al.

(10) Patent No.: US 8,153,742 B2
(45) Date of Patent: Apr. 10, 2012

(54) ACRYLIC POLYMER-BASED ADHESIVES

(75) Inventors: Allison Luciano, Lebanon, NJ (US);
Eric N. Silverberg, Summit, NJ (US);
Paul B. Foreman, Somerville, NJ (US);
Jianye Wen, Palo Alto, CA (US); Eli J. Goldman, San Francisco, CA (US); Jay Audette, Mountain View, CA (US)

(73) Assignee: Henkel AG & Co. KGaA, Duesseldorf (DE)

( * ) Notice: Subject to any disclaimer, the term of this patent is extended or adjusted under 35 U.S.C. 154(b) by 329 days.

(21) Appl. No.: 12/067,678

(22) PCT Filed: Sep. 22, 2006

(86) PCT No.: PCT/US2006/037067
§ 371 (c)(1),
(2), (4) Date: Mar. 21, 2008

(87) PCT Pub. No.: WO2007/038323
PCT Pub. Date: Apr. 5, 2007

(65) Prior Publication Data
US 2008/0243043 A1  Oct. 2, 2008

(51) Int. Cl.
*C08F 120/54* (2006.01)
(52) U.S. Cl. .............. 526/307.1; 526/307.5; 526/318.41
(58) Field of Classification Search ............... 526/307.1, 526/307.5, 318.41
See application file for complete search history.

(56) References Cited

U.S. PATENT DOCUMENTS

| | | | |
|---|---|---|---|
| 3,532,708 A | 10/1970 | Blance | |
| 4,079,030 A | 3/1978 | Takanen et al. | |
| 4,294,738 A | 10/1981 | Beresniewicz | |
| 5,326,644 A | 7/1994 | Scholz et al. | |
| 5,498,418 A | 3/1996 | Beulner et al. | |
| 6,083,856 A * | 7/2000 | Joseph et al. | 442/361 |
| 6,107,222 A * | 8/2000 | Joseph et al. | 442/412 |
| 6,198,016 B1 * | 3/2001 | Lucast et al. | 602/41 |
| 6,262,329 B1 * | 7/2001 | Brunsveld et al. | 602/54 |
| 2003/0022980 A1 | 1/2003 | Foreman et al. | |
| 2007/0072986 A1 | 3/2007 | Luciano et al. | |
| 2007/0082038 A1 | 4/2007 | Gale et al. | |
| 2007/0098771 A1 | 5/2007 | Audett et al. | |
| 2007/0098772 A1 | 5/2007 | Westcott et al. | |
| 2007/0104771 A1 | 5/2007 | Audett et al. | |
| 2007/0134310 A1 | 6/2007 | Nedberge et al. | |
| 2008/0275157 A1 | 11/2008 | Luciano et al. | |

FOREIGN PATENT DOCUMENTS

| | | |
|---|---|---|
| EP | 0501124 | 9/1992 |
| EP | 0518113 A | 12/1992 |
| GB | 1381185 A | 1/1975 |
| WO | 0210306 A2 | 2/2002 |

* cited by examiner

*Primary Examiner* — Bernard Lipman
(74) *Attorney, Agent, or Firm* — Sun Hee Lehman

(57) ABSTRACT

Acrylic polymers comprising a non-primary hydroxyl functional monomer and low Tg alkyl acrylate monomers are useful in adhesive compositions that find use in skin contact applications.

20 Claims, No Drawings

ACRYLIC POLYMER-BASED ADHESIVES

FIELD OF THE INVENTION

The invention relates to acrylic polymers and adhesive compositions, and end use applications thereof. In particular, adhesives which are ideally suited for skin contact applications.

BACKGROUND OF THE INVENTION

Pressure-sensitive adhesive (PSA) compositions are used for pressure-sensitive adhesive tapes, the adhesive tape comprising a backing and a PSA composition.

One field where PSA compositions find wide spread use is the medical segment, e.g., various tapes, bandages and drug delivery devices. In many such applications, such as for example skin plasters, there is direct contact between the PSA composition and the patient's skin. Adhesives for application to the skin are permanently tacky at room temperature, hold the adhered article to the skin with gentle pressure, and should be easily removed without causing pain or depositing adhesive residue.

In medical applications, the requirements imposed on the PSA composition are especially stringent, since it is necessary to avoid skin irritation and allergic reaction. Moreover, such adhesives need to adhere well to human skin during perspiration, when the weather is hot, or in an environment of draining wounds.

The continuous controlled delivery of drugs through the derma, i.e., skin, provides many advantages over other routes of administration. Transdermal drug delivery is a comfortable, convenient, and noninvasive alternative to other means of drug delivery such as by ingesting medication at fixed time intervals orally or by way of subcutaneous injection. Transdermal drug delivery systems not only allow the controlled release of a pharmaceutical product in a sustained release fashion, but reduce side effects such as gastrointestinal irritation, avoid hepatic first-pass inactivation, poor or erratic absorption from the gastrointestinal tract, and inactivation by the gastrointestinal fluids. Transdermal drug delivery also makes possible a high degree of control over blood concentrations of any particular drug. These advantages enhance patient compliance and improve the safety and efficacy of medications.

In transdermal drug delivery systems, drugs are delivered from a patch applied to the skin with a pressure sensitive adhesive. The known advantages of continuous transdermal drug delivery devices has prompted the development of transdermal drug delivery systems for the administration of a variety of drugs.

While acrylic adhesives for application to the skin are known, there is an ongoing demand and continuing need in the art for PSAs useful in medical applications. The current invention addresses this need in the art.

SUMMARY OF THE INVENTION

The invention provides polymers and adhesive compositions that can be formulated for use in medical applications, including transdermal drug delivery systems.

One aspect of the invention is directed to polymers comprising less than about 50 wt % of a functional monomer component and greater than about 40 wt % of a low Tg alkyl acrylate component, and wherein the polymer comprises greater than about 3 wt % of a non-primary hydroxyl functional monomer.

Another aspect of the invention is directed to compositions comprising the polymers, including pressure sensitive adhesives for use in medical applications. The adhesive may be used in the manufacture of articles such as plasters, bandages and tapes which are adhesively adhered to the skin. The adhesive is permanently adhered to at least one substrate of the article and removable or releasably attachable to skin.

The adhesive compositions comprise acrylic polymers comprising less than about 50 wt % of a functional monomer component and greater than about 40 wt % of a low Tg alkyl acrylate component, and wherein the polymer comprises greater than about 3 wt % of a secondary hydroxyl functional monomer. One preferred embodiment the adhesive comprises acrylic polymers containing butyl acrylate, t-octyl acrylamide, hydroxypropyl acrylate and acrylic acid. The adhesive compositions may further comprise tackifiers, plasticizers, permeation enhancers and/or therapeutic agents. The therapeutic agent, while physiologically active, may or may not be pharmaceutically active.

Yet another aspect of the invention provides articles such as plasters, bandages and tapes to be adhesively adhered to the skin. The articles comprise a backing substrate having coated to at least one surface thereof an adhesive. In one embodiment the article comprising a pressure sensitive adhesive and a therapeutic agent. In a preferred embodiment, the adhesive serves as a carrier for the physiologically active agent.

Still another aspect of the invention is directed to a method of administering a therapeutic agent to a patient comprising applying to a body surface of the patient an article comprising a backing substrate having coated to at least one surface thereof a pressure sensitive adhesive and a physiologically active agent. In one embodiment the article includes an adhesive layer into which the drug to be delivered is incorporated, a distal backing layer and a proximal release layer.

DETAILED DESCRIPTION OF THE INVENTION

Percent by weight means, unless expressly stated otherwise, percent dry weight.

The acrylic polymer of the invention comprises at least one non-primary hydroxyl functional monomer component and a low Tg alkyl acrylate monomer component. It has been discovered that polymers comprising greater than about 3 wt % of a secondary hydroxyl functional monomer and a low Tg alkyl acrylate monomer component are particularly well suited for use in adhesive compositions that can be used in the production of adhesive goods such as, for example, adhesive tapes and adhesive sheets by applying an adhesive or adhesive composition to a base material such as paper, cloth or plastic film. Preferred polymers comprise butyl acrylate, t-octyl acrylamide, hydroxypropyl acrylate and acrylic acid.

The acrylic polymer will comprise one or more non-primary hydroxy monomers, including secondary and/or tertiary hydroxyl functional monomers. Examples include hydroxypropyl acrylate and hydroxypropyl methacrylate. The polymers of the invention comprise greater than about 3 wt %, preferably greater than about 5 wt %, more typically greater than about 15 wt % of a non-primary hydroxyl functional monomer. Amounts up to about 40 wt % may be used. Such monomers are available commercially from BASF and Dow Chemical Company. Commercial sources of non-primary functional monomers will typically contains small amounts, usually less that 5%, more typically less 2% of primary functional monomers.

Other carboxy and/or hydroxy functional monomers, including primary functional monomers, may be used if desired. Useful carboxylic acids preferably contain from about 3 to about 6 carbon atoms and include, among others, acrylic acid, methacrylic acid, itaconic acid, β-carboxyethyl acrylate and the like. Acrylic acid, methacrylic acid and mixtures thereof are particularly preferred. Examples of hydroxy functional monomers include hydroxyethyl acrylate, hydroxypropyl acrylate, hydroxyethyl methacrylate and hydroxypropyl methacrylate. Such hydroxy and/or carboxy functional monomers are generally used in amounts up to about 25 wt %, more typically from about 5 to about of 10 wt %, based on the total monomer weight of the acrylic polymer.

The acrylic polymer will also comprise at least one low glass transition temperature (Tg) alkyl acrylate monomer. Low Tg monomers are those having a homopolymer Tg of less than about 0° C. Preferred alkyl acrylates which may be used to practice the invention have up to about 18 carbon atoms in the alkyl group, preferably from about 4 to about 10 carbon atoms in the alkyl group. Alkyl acrylates for use in the invention include methyl acrylate, butyl acrylate, amyl acrylate, hexyl acrylate, 2-ethylhexyl acrylate, octyl acrylate, isooctyl acrylate, decyl acrylate, dodecyl acrylates, isomers thereof, and combinations thereof. Particularly preferred are butyl acrylate, 2-ethylhexyl acrylate and/or isooctyl acrylate, most preferably 2-ethylhexyl acrylate.

The low Tg acrylic monomers are present in amounts greater than about 40 wt %, more preferably in amounts of from about 55 to 65 wt %, based upon the total monomer weight of the acrylic polymer.

The adhesives may desirable also contain a nitrogen containing compound, in particularly N-substituted acrylamides or methacrylamides. Examples include N-vinyl pyrrolidone, N-vinyl caprolactam, N-tertiary octyl acrylamide (t-octyl acrylamide), dimethyl acrylamide, diacetone acrylamide, N-tertiary butyl acrylamide (t-butyl acrylamide and N-isopropyl acrylamide (i-propyl acrylamide).

The acrylic polymer may optionally further comprise other well known comonomers including monomers having a high glass transition temperature (i.e., a Tg greater than about 0° C.). Non-limiting examples include methyl acrylate, ethyl acrylate, isobutyl methacrylate and/or vinyl acetate. Other comonomers can be used to modify the Tg of the acrylic polymer. Such comonomers include N-vinyl pyrrolidone, N-vinyl caprolactam, N-alkyl (meth)acrylamides such as t-octyl acrylamide, cyanoethylacrylates, diacetoneacrylamide, N-vinyl acetamide, N-vinyl formamide, glycidyl methacrylate and allyl glycidyl ether.

The adhesive compositions of the present invention optionally may include other monomers such as vinyl acetate and styrene, alkyl methacrylates such as methyl methacrylate and alkyl dimethacrylates.

Adhesives of the invention may also comprise blended polymers wherein the acrylic polymer is blended with and further comprises other types of polymers, including silicone polymers such as polydimethylsiloxane and polymethylphenylsiloxane and rubber polymers such as polyiso-butylene and styrene-isoprene-styrene block copolymer.

In a particularly preferred embodiment, the acrylic polymer comprises from about 55 to about 65 wt % of butyl acrylate, from about 5 to about 15 wt % t-octyl acrylamide, from about 20 to about 30 wt % of hydroxypropyl acrylate and from about 5 to about 10 wt % of acrylic acid. One embodiment comprises about 59 wt % of butyl acrylate, about 9.5 wt % t-octyl acrylamide, about 25.5 wt % of hydroxypropyl acrylate and about 6 wt % of acrylic acid.

While a particular polymerization method is described in the examples, the polymer of the present invention may be prepared by conventional polymerization methods familiar to those of skill in the art. These methods include, without limitation solution polymerization, suspension polymerization, bulk polymerization and emulsion polymerization. In the practice of the invention, it may also be advantageous to reduce the residual monomer content, or remove or reduce solvent levels and/or other volatiles, following polymerization using methods which are known and conventional in the art. Adhesive may be applied from organic solution, aqueous dispersion, or from a melt.

As used herein, the term "pressure-sensitive adhesive" refers to a viscoelastic material which adheres instantaneously to most substrates with the application of slight pressure and remains permanently tacky. A polymer is a pressure-sensitive adhesive within the meaning of the term as used herein if it has the properties of a pressure-sensitive adhesive per se or functions as a pressure-sensitive adhesive by admixture with tackifiers, plasticizers or other additives.

Suitable tackifying agents are those known in the art including: (1) aliphatic hydrocarbons; (2) mixed aliphatic and aromatic hydrocarbons; (3) aromatic hydrocarbons; (4) substituted aromatic hydrocarbons; (5) hydrogenated esters; (6) polyterpenes; (7) mineral oils; and (8) wood resins or rosins and hydrogenated forms thereof. Levels of tackifiers is generally from about 1 wt % to about 30 wt % based on the weight of the total adhesive composition.

The compositions of the invention may include other additives known to those skilled in the art. These additives may include, but are not limited to, pigments, fillers, fluorescent additives, flow and leveling additives, wetting agents, surfactants, antifoaming agents, rheology modifiers, permeation enhancers, stabilizers, and antioxidants.

Antioxidants are typically added singly or in combination to protect the ingredients against degradation during preparation and use of the adhesive compositions and to ensure long-term thermal stability. In general up to about 1% by weight of one or more antioxidants is included in the adhesive compositions. Usually, from about 0.1% to about 0.5% by weight.

While the pressure sensitive adhesive of the invention may be used in any number of applications, e.g., labels, the adhesive is particularly well-suited for use in medical applications. The pressure sensitive adhesives find use in the manufacture of articles such as ostomy seals, adhesive tapes and bandages, wound drainage adhesive seals, wound dressings, as adherents for other products and the like that adhere to human skin and remain adherent even in a moist environment.

The adhesive of the invention is particularly well-suited for use in transdermal applications. The pressure sensitive adhesive of the invention may be incorporated into a transdermal drug delivery device designed to deliver a therapeutically effective amount of a product to the skin of a patient, e.g., to cure a skin irritation or to deliver a therapeutically effective amount of drug across the skin of a patient. The term transdermal refers to the use of the skin as a portal for the administration of drugs by topical application or for diagnostic procedures such as the monitoring of blood chemistry. The topically applied drug passes into and/or through the skin. Thus "transdermal" is used broadly to refer to the topical administration of a drug which acts locally, i.e., at the surface or within the skin, such as, for example, a blemish patch used to treat acne, and to the topical application of a drug which acts systemically by diffusing through the skin and entering the blood stream.

Transdermal drug delivery devices of the invention comprise a carrier (such as liquid, gel, or solid matrix, or a pressure sensitive adhesive) into which the drug to be delivered is incorporated, a distal backing layer and a proximal release layer. When the patient peels the release liner from the adhesive and applies the patch, the drug partitions into the stratum corneum (outer skin layer) and permeates through the epidermis and dermis.

The pressure-sensitive skin contact adhesive of the invention. The adhesive of the invention may be used as a carrier contact adhesive or overlay contact adhesive for transdermal patches and is non-irritating, easy to apply, and easy to remove.

The term "drug" is to be construed herein in its broadest sense to mean any agent which is intended to produce some therapeutic benefit. The agent may or may not be pharmaceutically active, but will be "bioactive" in the sense that it has an effect on the human body. The agent may be used to treat or alter a condition, which may or may not be a pathological, i.e., a disease state. "Drug", "bioactive agent," "preparation," "medicament," "therapeutic agent," "physiological agent" and "pharmaceutical agent" are used interchangeably herein and include substances for use in the diagnosis, cure, mitigation, arrest, treatment or prevention of a condition or disease state or to affect the structure or function of the body. Skin-wellness agents that function to e.g., soften and moisturize are included in this term. The term "treatment" is used broadly to encompass prevention, alteration, cure and control of the condition.

The drug is present in a drug delivery device of the invention in a therapeutically effective amount, i.e., an amount effective to bring about a desired therapeutic result in the treatment of a condition to which the preparation of this invention is to be applied. Effective amount of a drug means a nontoxic but sufficient amount of a drug to provide the selected effect over a specific period of time. The amount that constitutes a therapeutically effective amount varies according to the particular drug incorporated in the device, the condition being treated, any drugs being co-administered with the selected drug, desired duration of treatment, the surface area of the skin over which the device is to be placed, and other components of the drug delivery device. Such an amount is readily determinable by the skilled practitioner.

The drug delivery system of the invention, in addition to the drug, may advantageously also contain an effective amount of a penetration enhancer. An effective amount of a penetration enhancer means an amount that provides a selected increase in membrane permeability, rate of administration and amount of drug.

The device of the invention is placed on the skin and allowed to remain for a time sufficient to achieve or maintain the intended therapeutic effect. The time that constitutes a sufficient time can be selected by those skilled in the art with consideration of the flux rate of the device of the invention and of the condition being treated.

The transdermal delivery devices of the invention can be made in the form of an article such as a tape, a patch, a sheet, a dressing or any other form known to those skilled in the art. The dosage system may be produced in any desirable unit form. A circular form is convenient as it contains no corners which might be easily detached from the skin. In addition to having various shapes, the dosage units produced may come in various sizes.

Depending on the design of the patch and the condition to be treated (e.g., birth control, pain management, hypertension, smoking cessation, skin condition), the patch will remain on the skin for up to an hour or more, up to about one week. In a preferred embodiment, the patch is designed to remain on the skin at the application site for about 24 hours, and to be changed daily. Preferably, the patch will be placed on the skin at a site different from the location of the previously used patches.

The term patient is used herein to include animals, both human and non-human, including companion animals such as dogs, cats and horses and livestock such as cattle and swine. Agricultural and horticultural applications are also contemplated.

Drugs that can be included in the carrier of the invention include substances capable of a local or a systemic effect when administered to the skin. Non-limiting examples include nicotine, testosterone, estradiol, salicylic acid, vitamin E, and nitroglycerin.

Veterinary drugs may also be conveniently applied using the transdermal drug delivery device of the invention, as well as agricultural and horticultural agents. It will be appreciated that transdermal drug delivery in veterinary and horticultural applications enables more exact dosing, and less waste than administration in the food/irrigation water.

A drug delivery device of the invention can be prepared by using conventional methods to apply an appropriate carrier to the backing. For example, a matrix device can be manufactured by preparing a coating formulation by mixing a solution of the adhesive in a solvent with the drug and any excipients to form a homogeneous solution or suspension; applying the formulation to a substrate (a backing or a release liner) using well known knife or bar or extrusion die coating methods; drying the coated substrate to remove the solvent; and laminating the exposed surface to a release liner or backing.

The invention will be described further in the following examples, which are included for purposes of illustration and is not intended, in any way, to be limiting of the scope of the invention.

EXAMPLES

Example 1

Four samples that are representative of the invention are set forth in Table 1. Example 2 details how the polymer of Sample 2 was made.

TABLE 1

| Monomers (wt %) | Sample 1 | Sample 2 | Sample 3 | Sample 4 |
|---|---|---|---|---|
| Butyl acrylate | 75 | 59 | 47.5 | 62.5 |
| 2-Hydroxypropyl acrylate | 5 | 25.5 | 40 | |
| 2-Hydroxypropyl methacrylate | | | | 31.5 |
| Acrylic acid | 3 | 6 | 3 | 6 |
| t-octyl acrylamide | 17 | 9.5 | 9.5 | |
| Tg (C.) | −26 | −25 | −19 | −18 |
| % Solids | 34.2 | 35.2 | 34.5 | 34.6 |
| Viscosity (cP) | 315 | 1400 | 1420 | 1080 |
| Relative viscosity | 2.31 | 2.85 | 2.91 | 2.79 |

Example 2

An initial charge containing 58.51 g butyl acrylate, 25.21 g 2-hydroxypropyl acrylate, 9.37 g t-octyl acrylamide, 5.94 g acrylic acid, 132.0 g ethyl acetate (solvent), and 0.17 g 2,2'-azobisisobutyronitrile (AIBN) (polymerization initiator) was prepared and charged to a 2-L 4-neck round bottom flask equipped with stainless steel stirrer, thermometer, condenser, water bath, and slow addition funnels. The initial charge was heated to reflux while stirring. At 15 minutes from the start of reflux, monomer mix containing 136.22 g butyl acrylate, 58.97 g 2-hydroxypropyl acrylate, 21.98 g t-octyl acrylamide, 13.86 g acrylic acid, and 165.0 g ethyl acetate were simultaneously and uniformly added over a period of 3 hours. Also at 15 minutes from the start of reflux, 51.15 g ethyl acetate and 1.98 g AIBN were simultaneously and uniformly added over a period of 4 hours. At the end of the addition, the flask contents were held at reflux for 1 hour. At 315 minutes from the start of reflux, 49.50 g ethyl acetate was added over a period of 2 hours. At the end of the addition, the flask contents were held at reflux for 1 hour. At the end of the hold period, the contents were cooled to room temperature and the solution polymer discharged.

The invention claimed is:

1. An acrylic polymer comprising less than about 50 wt % of a non-primary hydroxyl functional monomer and greater than about 40 wt % of a low Tg alkyl acrylate monomer, and wherein the polymer comprises greater than about 3 wt % of a secondary hydroxyl functional monomer.

2. The polymer of claim 1 further comprising a nitrogen containing monomer and/or a carboxyl functional monomer.

3. The polymer of claim 2 which comprises hydroxypropyl acrylate and/or hydroxypropyl methacrylate.

4. The polymer of claim 3 which comprises butyl acrylate, t-octyl acrylamide, hydroxypropyl acrylate and acrylic acid.

5. An acrylic polymer comprising from about 55 to about 65 wt % of butyl acrylate, from about 5 to about 15 wt % t-octyl acrylamide, from about 20 to about 30 wt % of hydroxypropyl acrylate that is a non-primary hydroxyl functional monomer, and from about 5 to about 10 wt % of acrylic acid.

6. The polymer of claim 5 which comprises about 59 wt % of butyl acrylate, about 9.5 wt % t-octyl acrylamide, about 25.5 wt % of hydroxypropyl acrylate and about 6 wt % of acrylic acid.

7. A pressure sensitive adhesive composition comprising an acrylic polymer, wherein the acrylic polymer comprises less than about 50 wt % of a non-primary hydroxyl functional monomer and greater than about 40 wt % of a low Tg alkyl acrylate, and wherein the polymer comprises greater than about 3 wt % of a secondary hydroxyl functional monomer.

8. The adhesive of claim 7 wherein the acrylic polymer comprises hydroxypropyl acrylate and/or hydroxylpropyl methacrylate.

9. The adhesive of claim 8 wherein the acrylic polymer also comprises a nitrogen containing monomer and/or a carboxyl functional monomer.

10. The adhesive of claim 9 wherein the alkyl acrylate monomer comprises butyl acrylate, 2-ethylhexyl acrylate and/or isooctyl acrylate.

11. The adhesive of claim 10 which comprises an N-substituted acrylamide.

12. The adhesive of claim 11 wherein the N-substituted acrylamide is t-octyl acrylamide.

13. The adhesive of claim 12 wherein the acrylic polymer comprises butyl acrylate, t-octyl acrylamide, hydroxypropyl acrylate and acrylic acid.

14. A transdermal drug delivery system comprising a pressure sensitive adhesive wherein the wherein the pressure sensitive adhesive comprises an acrylic polymer which comprises from about 55 to about 65 wt % of butyl acrylate, from about 5 to about 15 wt % t-octyl acrylamide, from about 20 to about 30 wt % of hydroxypropyl acrylate that is a non-primary hydroxyl functional monomer, and from about 5 to about 10 wt % of acrylic acid.

15. The adhesive of claim 14 further comprising a plasticizer, a tackifier, a permeation enhancer, a therapeutic agent, or a combination thereof.

16. An article of manufacture comprising the adhesive of claim 14.

17. The article of claim 16 to be adhesively adhered to the skin.

18. The article of claim 16 which is a tape, a plaster, or a bandage.

19. The article of claim 16 wherein the adhesive comprises an acrylic polymer comprising butyl acrylate, t-octyl acrylamide, hydroxypropyl acrylate and acrylic acid.

20. The article of claim 19 wherein the adhesive further comprises a plasticizer, a tackifier, a permeation enhancer, a therapeutic agent, or a combination thereof.

* * * * *